(12) United States Patent
Kulkarni et al.

(10) Patent No.: US 9,265,711 B2
(45) Date of Patent: Feb. 23, 2016

(54) COSMETIC COMPOSITION WITH WATERTIGHT FRAGRANCE

(71) Applicant: COTY B.V., Haarlem (NL)

(72) Inventors: Rupali A. Kulkarni, Bridgewater, NJ (US); Leslie C. Smith, Princeton, NJ (US); William Kopf, Mine Hill, NJ (US); Lisa D. Gilliam, Scotch Plains, NJ (US); Ralph Macchio, Sparta, NJ (US)

(73) Assignee: COTY B.V., Haarlem (NL)

( * ) Notice: Subject to any disclaimer, the term of this patent is extended or adjusted under 35 U.S.C. 154(b) by 151 days.

(21) Appl. No.: 13/796,659

(22) Filed: Mar. 12, 2013

(65) Prior Publication Data

US 2013/0209385 A1    Aug. 15, 2013

Related U.S. Application Data

(63) Continuation of application No. 13/014,831, filed on Jan. 27, 2011, now abandoned, which is a continuation of application No. 11/362,512, filed on Feb. 27, 2006, now abandoned, which is a continuation of application (Continued)

(30) Foreign Application Priority Data

Jan. 27, 2004    (DE) .................. 10 2004 005 095

(51) Int. Cl.
*A61K 8/02* (2006.01)
*A61K 8/97* (2006.01)
(Continued)

(52) U.S. Cl.
CPC ................. *A61K 8/8158* (2013.01); *A61K 8/37* (2013.01); *A61K 8/922* (2013.01); *A61Q 13/00* (2013.01); *A61Q 15/00* (2013.01); *A61Q 19/10* (2013.01)

(58) Field of Classification Search
CPC ......... A61Q 1/00; A61Q 19/00; A61Q 13/00; A61Q 15/00; A61Q 19/10; A61K 8/8152; A61K 8/8158; A61K 8/92; A61K 8/96; A61K 8/922; A61K 8/8141; A61K 2800/56; A61K 2800/57
See application file for complete search history.

(56) References Cited

U.S. PATENT DOCUMENTS 5,989,529 A    11/1999    Kaplan
6,027,739 A    2/2000    Nichols
(Continued)

FOREIGN PATENT DOCUMENTS

DE    10002107    8/2001
DE    10108387    8/2002
(Continued)

OTHER PUBLICATIONS

Cummings, "Built to last: A new jojoba derivative has been found to have impressive substantivity properties in a wide range of formulation types," J. Soap, Perfumery & Cosmetics (2001) 74: 42-45.

(Continued)

*Primary Examiner* — Lakshmi Channavajjala
(74) *Attorney, Agent, or Firm* — Novak Druce Connolly Bove + Quigg LLP

(57) ABSTRACT

The present invention refers to a cosmetic composition which, in particular, enables the perfume component resist wash off by water and sweat and to remain fixed on the skin for a long time watertightly. The cosmetic composition comprises fragrance and a fragrance-fixing complex consisting of 0.01-10% by weight of a hydrophobic, alcohol-soluble, carboxylated acrylates/octylacrylamide copolymer and 0.01-10% by weight of a hydrolyzed jojoba ester. Further the complex is able to significantly reduce the total amount of fragrances while giving the same scent feeling to the consumer.

22 Claims, 4 Drawing Sheets

Related U.S. Application Data

No. PCT/EP2005/000931, filed on Jan. 26, 2005, now abandoned.

(60) Provisional application No. 60/600,018, filed on Aug. 9, 2004.

(51) Int. Cl.

| | |
|---|---|
| *A61K 8/84* | (2006.01) |
| *A61K 8/81* | (2006.01) |
| *A61K 8/92* | (2006.01) |
| *A61Q 13/00* | (2006.01) |
| *A61K 8/37* | (2006.01) |
| *A61Q 15/00* | (2006.01) |
| *A61Q 19/10* | (2006.01) |

(56) References Cited

U.S. PATENT DOCUMENTS

| | | |
|---|---|---|
| 6,143,353 A | 11/2000 | Oshlack et al. |
| 6,172,037 B1 | 1/2001 | Perring et al. |
| 6,190,681 B1 | 2/2001 | Fishman |
| 6,287,579 B1 | 9/2001 | Kleiman et al. |
| 7,041,278 B2 | 5/2006 | Barone et al. |
| 7,323,162 B2 | 1/2008 | Martin et al. |
| 2002/0192174 A1 | 12/2002 | Kawakami et al. |
| 2004/0028641 A1 | 2/2004 | Barone et al. |
| 2004/0146477 A1 | 7/2004 | Meffert et al. |
| 2004/0265343 A1 | 12/2004 | Hill |
| 2009/0191243 A9 | 7/2009 | Hill |

FOREIGN PATENT DOCUMENTS

| | | |
|---|---|---|
| EP | 1133973 A1 | 9/2001 |
| EP | 0710114 B1 | 2/2003 |
| EP | 1715841 B1 | 5/2007 |
| WO | 0149257 | 7/2001 |
| WO | 2005004831 A1 | 1/2005 |
| WO | 2005070371 | 8/2005 |

OTHER PUBLICATIONS

Final Office Action (USPTO) mailed on Oct. 28, 2010 in U.S. Appl. No. 11/362,512. (10 pages).
Final Office Action (USPTO) mailed on Sep. 14, 2012 in U.S. Appl. No. 13/014,831. (15 pages).
International Preliminary Report on Patentability mailed on Jul. 27, 2006 in International Application No. PCT/EP2005000931, International Filing Date Jan. 26, 2005. (5 pages).
International Search Report and the Written Opinion of the ISA mailed on Jul. 27, 2006 in International Application No. PCT/EP2005000931, International Filing Date Jan. 26, 2005. (5 pages).
Non Final Office Action (USPTO) mailed on Mar. 25, 2010 in U.S. Appl. No. 11/362,512. (8 pages).
Non Final Office Action (USPTO) mailed on Mar. 29, 2012 in U.S. Appl. No. 13/014,831. (10 pages).
Non Final Office Action (USPTO) mailed on May 22, 2009 in U.S. Appl. No. 11/362,512. (10 pages).
"Spray 'N Go Sunblock" data sheet (2003), Floratech

COSMETIC COMPOSITION WITH WATERTIGHT FRAGRANCE

CROSS REFERENCE TO RELATED APPLICATIONS

This Continuation Application is a Continuation of U.S. patent application Ser. No. 13/014,831, filed Jan. 27, 2011, which is a continuation application of U.S. application Ser. No. 11/362,512 filed Feb. 27, 2006 which claims priority to International Application No. PCT/EP2005/000931 filed Jan. 26, 2005, which claims priority to German Application No. DE 10 2004 005 095.3 filed Jan. 27, 2004 and to U.S. Provisional Application No. 60/600,018, filed Aug. 29, 2004, all of which are incorporated by reference in their entirety herein.

The present invention refers to a cosmetic composition which, in particular, enables the perfume component to resist wash off by water and sweat and to remain fixed on the skin for a long time (fragrance-watertight composition).

It is known to encapsulate perfume oils in liposomes or cyclodextrins to achieve a controlled release of these oils. Several systems have also been used to improve bonding to the skin or to extend the time the perfume lasts, e.g. chitin derivatives, quaternary chitosans, silicate materials and thermoplastic polyamides.

U.S. Pat. No. 6,143,353 A discloses the coating of pharmaceutically active ingredients as well as fragrant components with an aqueous dispersion of a plasticized, hydrophobic acrylic polymer, which acrylic polymer is an (alkyl) ester of acrylic/methacrylic acid.

U.S. Pat. No. 6,172,037 B1 discloses perfume-fixing substances comprising polyvinylpyrrolidone, hydroxy-propyl cellulose and a hydrophobic oil.

The object of the present invention is to provide a cosmetic composition which is wash-off resistant by water and at the same time ensures that the perfume component remains fixed on the skin for a long time.

A further object of the invention is to provide a cosmetic composition with reduced fragrance content and a feeling of the fragrance by the consumer without any difference.

According to the invention, the cosmetic composition comprising fragrances is further comprising a fragrance-fixing complex which comprises
0.01 to 10% by weight of a hydrophobic, alcohol-soluble, carboxylated acrylates/octylacrylamide copolymer,
0.01 to 10% by weight of a hydrolyzed jojoba ester,
and where all percents are related to the total weight of the cosmetic composition.

The range of fragrances is between 0.01 and 35% by weight. A preferred range is 0.1-16%, more preferred 0.5-8% by weight, most preferred 1 to 5% by weight.

It is preferred that the copolymer be contained in an amount ranging between 0.1 and 5% by weight, more preferred 0.1-1.0% by weight. The carboxylated acrylates/octylacrylamide copolymer can be replaced by the acrylic polymer Dermacryl® AQF (National Starch & Chemical Co., Bridgewater N.J., USA).

Further it is preferred that the jojoba ester is present in a range of 0.1 to 5%, more preferred 0.1-1% by weight.

In a special embodiment of the invention the jojoba ester and the copolymer constitute a separately prepared complex in the relation 1:1-4, preferably 1:1.2-2.8 of jojoba ester: polymer.

In a further embodiment of the invention the cosmetic composition comprises an alcohol or alcohol/water mixture.

The aforesaid fragrance-fixing complex can be used in cosmetic products such as emulsions, creams, lotions, sprays, shower gels, shower oils, bath products, foam baths, perfumes, aftershaves, shaving balms, face lotions, hair conditioners, skin gels, deodorants, detergents etc. At the same time, further cosmetic auxiliaries and carrier substances as they are commonly used in such preparations can be used, as well as further active agents. Auxiliaries include e.g. preservatives, colourants, polyols, esters, electrolytes, gel-forming agents, polar and non-polar oils, polymers, further copolymers, stabilizers, surface-active agents.

Cosmetic active agents include e.g. organic sunscreens, scavengers, moisturizing substances, vitamins, enzymes, plant-based active agents, polymers, antioxidants, anti-inflammatory natural active agents.

Preferred cosmetic fragrances are oil-soluble fragrances such as all fragrance oils which are known for the skilled in the art.

The hydrophobic, alcohol-soluble, carboxylated acrylates/octylacrylamide copolymer used according to the invention is soluble in ethanol, isopropanol and fatty alcohols. It can be made water-soluble or dispersible in water by neutralizing the carboxy groups with water-soluble bases such as triethanolamine, sodium carbonate, aminomethylpropanol, potassium hydroxide or ammonium hydroxide. It can thus be easily washed off the skin with soap, if necessary. Due to the interaction of the copolymer with the hydrolyzed jojoba ester, which ester is soluble in the aqueous-alcoholic system and in glycol, and the solvent, fragrant molecules are integrated into a complex and remain bonded to the skin for a very long time. At the same time, the aforesaid complex has a strong water-repellent effect. Thus a very good endurance of the fragrant molecules on the skin is achieved during rain, sweat, swimming, etc.

A preferred copolymer is Acrylates Octylacrylamide Copolymer with an acidity of 2.4 meq/g. Such a product is available under DERMACRYL®AQF or DERMACRYL®79 by National Starch and Chem. Comp., NJ, USA.

A preferred hydrolyzed jojoba ester is one of plant origin (*Simmondsia chinensis*) having a saponification value according to AOCS Cd 3-25* of max. 1 mg KOH/g, a iodine value according to AOCS Cd 1d-92* of between 14 and 17 g/100 g and a trans isomer value according to AOCS Cd 14-95* of max. 0.1% by weight (* test procedure according to American Oil Chemists Society). Such a product (INCI: Hydrolyzed Jojoba Esters (and) Water) is available under Floraesters® K-20W Jojoba by Int. Floratech Technol. Ltd., Hartsdale, N.Y., USA.

The following substances are particularly suitable for further processing the cosmetic complex.

Oils: Silicone oils, mineral oils, Hydrogenated Polyisobutene, Polyisoprene, Squalane, Tridecyl Trimellitate, Trimethylpropane Triisostearate, Isodecyl Citrate, Neopentyl Glycol Diheptanoate, PPG-15 Stearyl Ether as well as vegetable oils such as Calendula Oil, Jojoba Oil, Avocado Oil, Macadamia Nut Oil, Castor Oil, Cocoa Butter, Coconut Oil, Maize Oil, Cottonseed Oil, Olive Oil, Palm Kernel Oil, Rapeseed Oil, Safflower Oil, Sesame Seed Oil, Soybean Oil, Sunflower Seed Oil, Wheatgerm Oil, Grapeseed Oil, Kukui Nut Oil, Thistle Oil, and mixtures thereof. Synthetic squalane or squalane made from natural products is suitable too, as well as cosmetic esters or ethers which can be branched or linear, saturated or unsaturated.

Scavengers: Antioxidants, vitamins such as Vitamin C and derivatives thereof, e.g. ascorbyl acetate, ascorbyl phosphate and ascorbyl palmitate; Vitamin A and derivatives thereof; folic acid and derivatives thereof; Vitamin E and derivatives thereof such as tocopheryl acetate; flavones and flavonoids;

amino acids such as histidine, glycine, tyrosine, tryptophan and derivatives thereof; carotenoids and carotenes such as α-carotene, β-carotene; uric acid and derivatives thereof; α-hydroxy acids such as citric acid, lactic acid, malic acid.

Moisturizing substances: Glycerine, Butylene Glycol, Propylene Glycol, and mixtures thereof.

Organic sunscreens: Derivatives of 4-aminobenzoic acid such as 4-(dimethylamino)-benzoic acid-(2-ethylhexyl)ester; esters of cinnamic acid such as 4-methoxy cinnamic acid(2-ethylhexyl)Ester; benzophenone derivatives such as 2-Hydroxy-4-methoxy benzophenone; derivatives of 3-benzylidene camphor such as 3-Benzylidene Camphor. Other preferred oil-soluble UV filters are Benzophenone-3, Butyl Methoxybenzoylmethane, Octyl Methoxycinnamate, Octyl Salicylate, 4-Methylbenzylidene Camphor, Homosalate, and Octyl Dimethyl PABA.

Surface-active agents: Anionic, amphoteric, non-ionic or cationic surface-active agents, or mixtures thereof. Cationic polymers or a mixture of anionic and amphoteric surface-active agents are particularly preferred.

Non-limiting examples of anionic foaming surface-active agents include those selected from the group consisting of alkyl sulphates, alkyl ether sulphates, sulphated monoglycerides, sulphonated olefins, alkyl aryl sulphonates, primary or secondary alkane sulphonates, alkyl sulphosuccinates, acyl taurates, acyl isothionates, alkyl glyceryl ether sulphonates, sulphonate methyl esters, sulphonated fatty acids, alkyl phosphates, acyl glutamates, acyl sarcosinates, alkyl sulpho-acetates, acylated peptides, alkyl ether carboxylates, acyl lactylates of anionic surface-active agents containing fluorine, and mixtures thereof. Mixtures of anionic surface-active agents can be effectively used in the present invention.

Examples of amphoteric surface-active agents which can be used in the present invention include at least those having an acid group. The aforesaid group can be a carboxyl group or a sulphonic acid group. Quaternary nitrogen and therefore quaternary amino acids are included. They should, in general, contain an alkyl group or alkenyl group having 7 to 18 carbon atoms. Suitable amphoteric detergents include simple betaines and amidobetaines which are a mixture of C12- and C14-alkyl groups derived from the coconut so that at least half, preferably three quarters, of the R1-hydrocarbon chain has 10 to 14 carbon atoms. It is preferred that the other two R2- and R3-hydrocarbon chains be methyl. Further, the amphoteric detergent can be a sulphobetaine. Amphoacetates and diamphoacetates can also occur as possible zwitterionic and/or amphoteric compounds, which can be used. An amphoteric surface-active agent should, in general, be contained in an amount ranging approximately between 0.1 and 20%, preferably 5 and 18% by weight, relative to the composition.

Suitable non-ionic surface-active agents include, but are not limited to, Coconut Acyl Mono-ethanolamide or Coconut Acyl Diethanolamide, Alkyl Polysaccharide, Lactobionamide, Ethylene Glycol Ester, Glycerine Monoether, Polyhydroxyamide (Glucamide), primary and secondary alcohol ethoxylates, particularly $C_{8-20}$ aliphatic alcohols ethoxylated with an average of 1 to 20 moles ethylene oxide per mole of alcohol. Mixtures of the aforesaid surface-active agents can also be used.

Pigments, pigment mixtures or powders with a pigment-like effect, also including those with a pearl-gloss effect may be added to the composition of the invention. The may include, for example, iron oxides, aluminum silicates such as ochre, titanium (di)oxide, mica, kaolin, manganese containing clays such as umber and red bole, calcium carbonate, French chalk, mica-titanium oxide, mica-titanium oxide-iron oxide, bismuth oxychloride, nylon beads, ceramic beads, expanded and non-expanded synthetic polymer powders, powdery natural organic compounds such as milled solid algae, milled plant parts, encapsulated and non-encapsulated cereal starches and mica-titanium oxide-organic dye.

Also included in the composition of the invention are antiperspirants and deodorants, such as Triclosan, Trimethyl Citrate, Farnesol, Aluminum Chlorhydrate, Aluminum Zirconium Tetrachlorhydex GLY etc.

In comparative tests, it has been found that the addition of the complex according to the invention brings about a significant increase in waterproofness during a period of 4-6 hours, both in a sensory test with test persons and in an analytical test by means of gas chromatography/mass spectroscopy. The waterproofness of an aftershave in a test lasting 8 hours was also considerably higher than that of the untreated original product.

It has further been found that the addition of the complex in the range of 0.5-8% by weight, preferably 1-3% by weight, related to the total weight of the cosmetic composition, e.g. a perfume, to the other ingredients of the cosmetic composition, can reduce the amount of the fragrance usually added to the composition without loss of fragrance intensity. This means that in consumer studies carried out to determine whether there was a difference in fragrance character between a standard product and a product with 20% less fragrance and added 1-2% of the complex of the invention, no significant difference has been stated.

The preferred method for manufacturing the waterproof cosmetic composition consists in that a hydrolyzed jojoba ester is mixed with some alcohol or alcohol/water mixture, and at a temperature ranging between 18-40° C. an acrylates/octylacrylamide copolymer in powder form is sprayed into the mixture during the mixing process. The received complex can dried before use in the cosmetic formulation or can directly added to the other ingredients of the composition. Mixing of some alcohol, the ester, the copolymer and optionally a 10% $Na_2CO_3$ solution in that order is also possible.

The use of the fragrance-fixing complex of the invention is preferred in the following groups of products
    perfumes
    hair care and body care products e.g. hair washes, body washes, shower gels, shampoos, conditioners, etc.
    sun care products e.g. sun creams, sun lotions, after-sun products, body bronzers, sun sprays, sun milks etc.
    antiperspirants and deodorants
    products of color cosmetic e.g. massacres, foundations, make-up, lipsticks, lip balms etc.

BRIEF DESCRIPTION OF DRAWINGS

The invention will hereinafter be explained in more detail by means of examples. The figures show

EXAMPLE 1

Aftershave

Figure 1:
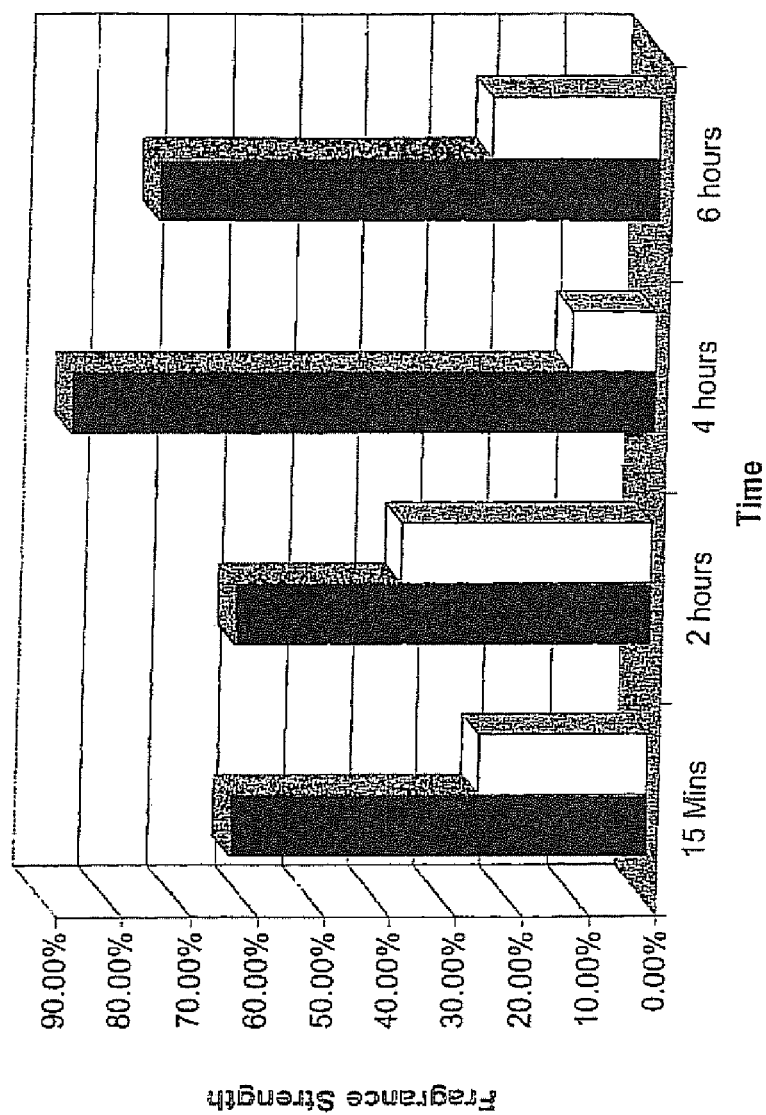
FIG. 1: Sensory analysis of aftershave of example 1

| Phase A | |
|---|---|
| Ethanol | q.s. ad 100 |
| Octyl Methoxycinnamate | 0.2 |
| Benzophenone-3 | 0.1 |
| PEG-60 Hydrogenated Castor Oil | 1.5 |
| L-Menthol | 0.15 |
| Phase B | |
| Fragrance | 7.0 |
| Ethanol | 15.0 |
| Phase C | |
| Water | 12 |
| Allantoin | 0.1 |
| Phase D | |
| Ethanol | 6.0 |
| Hydrolyzed Jojoba Esters & Water | 0.5 |
| Acrylates/Octylacrylamide Copolymer | 1.0 |
| Phase E | |
| Colourants | 0.015 |

The ingredients of Phase A were mixed with one another, incorporating PEG-60 Hydrogenated Castor Oil at approx. 60° C. Separately, Phases B and C were prepared in the same manner. Phase D was prepared by mixing the jojoba ester with ethanol at approx. 25° C. while spraying in the copolymer in powder form during the mixing process. The mixture was then stirred until a clear, homogeneous solution was obtained. First, Phase D was mixed with Phase B. Subsequently, Phases A and C were mixed with one another and the mixture was filtered using a filter cushion (60S). The mixture of Phases D and B was then added into the mixture of Phases A and C while stirring and finally Phase E was added and the overall mixture was stirred at a constant speed.

EXAMPLE 2

Antiperspirant Soft Solid

| | |
|---|---|
| Cyclomethicone and Dimethicone Crosspolymer | 32 |
| Stearyl Dimethicone | 1 |
| Hydrogenated Castor Oil | 1 |
| Cyclomethicone | ad 100 |
| Watertight complex* | 0.5 |
| Dimethicone | 15 |
| Aluminum Zirconium Tetrachlorohydrex GLY | 24 |

*²⁄₃ Acrylates/Octylacrylamide Copolymer
¹⁄₃ Hydrolyzed Jojoba Esters(and)Water

Weigh ingredients 1-5 into a vessel, heat to 80-85° C. and mix until waxes have melted and the mixture appears uniform. Remove from heat and add Dimethicone. The mixture will set at about 75° C. Add Al—Zr-Tetrachlorohydrex after mixture cools below 75° C. Continue mixing and cooling until the temperature is below 45° C.

EXAMPLE 3

Body Mist

| Phase A | |
|---|---|
| Alcohol | ad 100 |
| Fragrance | 4.5 |
| Phase B | |
| Water | 16 |
| White Ginger Extract | 0.1 |
| Phase C | |
| Alcohol | 1.5 |
| Watertight complex* | 0.5 |
| Phase D | |
| Colorant | 0.2 |

*see ex. 2

Mix alcohol and fragrance with agitation. Add phase B with agitation and mix until clear and uniform. Filter the main batch and add separate mixed phase C to the main batch with agitation. Add phase D and mix until uniform.

EXAMPLE 4

Clear Antiperspirant Gel (Female)

| Phase A | |
|---|---|
| Cyclomethicone | 2.5 |
| Dimethicone | 0.5 |
| Cyclopentasiloxane(and)PEG/PPG-18/18 Dimethicone | 7.5 |
| Triethyl Citrate | 0.1 |
| Farnesol | 0.05 |
| Phase B | |
| Aluminum Zirconium Tetrachlorohydrex GLY | 54 |
| Water | ad 100 |
| Allantoin | 0.1 |
| Polysorbate 80 | 0.5 |
| Dipropylene Glycol | 21 |
| Phase C | |
| Fragrance | 0.5 |
| Phase D | |
| Watertight complex* | 0.5 |

*see ex. 2

Mix phase A and B ingredients separately. If the refractive index of phase A is higher than of phase B, add some water to phase B. Add phase B to phase A very slowly while rapidly mixing phase A and homogenize. Add phase C and mix until uniform. Add phase D while agitation.

EXAMPLE 4A

A gel is prepared as in example 4 whereby the watertight complex comprises 0.5% Dermacryl® AQF and 0.25% Hydrolyzed Jojoba Esters.

EXAMPLE 5

Conditioner

| Phase A | |
|---|---|
| Water | ad 100 |
| Disodium EDTA | 0.02 |
| Phase B | |
| Steareth-20 | 1 |
| Dithicone Bisamino Hydroxypropyl Copolyol | 0.7 |
| Watertight complex* | 0.5 |
| Citric Acid | q.s. |
| Phase C | |
| Cetearyl Alcohol | 2 |
| Dipalmitoylethyldimonium Chloride | 3 |
| Glyceryl Stearate | 0.75 |
| Phase D | |
| Preservative | 0.5 |
| Fragrance | 1.5 |
| Sodium Hydroxide | q.s. |

*see ex. 2

Combine phase A ingredients with mixing and heat to 70° C., maintain temperature. Add with mixing phase B ingredients one by one to phase A, mix until uniform and adjust pH by citric acid. Combine phase C ingredients and heat to 70° C. and mix to main batch until uniform. Add individually phase D ingredients and adjust pH with sodium hydroxide.

EXAMPLE 6

Lotion

| Phase A | |
|---|---|
| Water | ad 100 |
| Disodium EDTA | 0.05 |
| Glycerine | 2 |
| Carbomer | 0.3 |
| Pemulan | 0.1 |
| Phase B | |
| Tribehenin | 1.3 |
| DC 200/500 | 1 |
| Stearoxytrimethylsilane(and)Stearyl Alcohol | 0.7 |
| Diisostearyl Dimer Dilinoleate | 6 |
| BHT | 0.05 |
| VP/Eicosene Copolymer | 1 |
| Potassium Cetyl Phosphate | 0.5 |
| Phase C | |
| Vitamin A Acetate | 0.5 |

-continued

| Phase D | |
|---|---|
| Water | 2 |
| Triethanolamine | 0.4 |
| Watertight complex* | 1.5 |
| Cyclomethicone | 1 |
| D Panthenol L | 1 |
| Phase E | |
| Water | 2 |
| Phenonip | 0.5 |
| Phase F | |
| Fragrance | 0.8 |

*see ex. 2

Mix water phase A ingredients separately and heat to 75-85° C. while mixing, maintain temperature. Mix phase B ingredients without Potassium Cetyl Phosphate (PCP) and heat to 75-80° C., add PCP until free of lumps. Add melted phase C ingredients (45-50° C.) to phase B and add phase B (75° C.) to phase A. Homogenize for 7-10 minutes. Add from phase D water and TEA at 65° C. and after than the complex. At 50° C. add Cyclomethicone and than Panthenol. Add phase E and F at 35° C. and cool to 30° C.

EXAMPLE 7

Shampoo

| Phase A | |
|---|---|
| Phylantriol&Disodium EDTA&Hydroxypropyl Guar&Hydroxypropyltrimonium Cloride& Tocopherylacetate (Miraspec KTS) | 55 |
| Phase B | |
| Fragrance | 1 |
| Phase C | |
| Plant extracts | 0.3 |
| Water | ad 100 |
| Watertight complex* | 1.8 |
| Phase D | |
| Colorant | 0.15 |
| Phase E | |
| Citric Acid (20% solution) | q.s. |
| Phase F | |
| Ammonium Chloride (20% solutione) | 2.4 |

*both ingredients 1:1

Mix separat prepared phases A and B. Add phase C ingredients while mixing. Add each ingredient of phase C separately to main main batch until clear and uniform. Continue mixing while adding phase D. Adjust pH with phase E if necessary. Add phase F while mixing.

EXAMPLE 8

Shower Gel

| Phase A | |
|---|---|
| Water | ad 100 |
| Disodium EDTA | 0.1 |
| Hydroxypropyl | 1 |

-continued

| | | |
|---|---|---|
| DMDM Hydantoin | | 0.3 |
| Phase B | | |
| Sodium Laureth Sulfate | | 10 |
| Disodium Laureth Sulfate | | 20 |
| Cocamidopropyl Betaine | | 9 |
| Phase C | | |
| Preservative | | 0.2 |
| Fragrance | | 2 |
| Dye | | 0.3 |
| Phase D | | |
| Sodium Chloride (20% solution) | | 0.8 |
| Phase E | | |
| Sodium Hydroxide (25% solution) | | q.s. |
| Phase F | | |
| Dermacryl ® AQF | | 0.5 |
| Hydrolyzed Jojoba Esters | | 0.25 |

Mix separat prepared phases A and B. Add phase C ingredients while mixing. Add each ingredient of phase C separately to main main batch until clear and uniform. Adjust viscosity with phase D and continue mixing. Adjust pH with phase E while mixing. Add phase F while mixing.

Beispiel 8a

A shower gel is prepared as in example 8 whereby the watertight complex comprises 0.5% Dermacryl® AQF and 0.25% Hydrolyzed Jojoba Esters.

EXAMPLE 9

Eau de Toilette

| | | |
|---|---|---|
| Phase A | | |
| Alcohol | | ad 100 |
| Fragrance | | 17 |
| Benzophenone-2 | | 0.1 |
| Phase B | | |
| Water | | 1.6 |
| Phase C | | |
| Colorant | | 0.3 |
| Phase D | | |
| Dermacryl ® AQF | | 5 |
| Hydrolyzed Jojoba Esters | | 2 |

The proceeding is according to example 11.

EXAMPLE 10

Perfume

| | |
|---|---|
| Alcohol | ad 100 |
| Fragrance | 20 |
| Benzophenone 2 | 0.1 |
| Water | 9 |
| Watertight complex* | 5 |
| Colorant | 1 |

*see ex. 2

EXAMPLE 11

Eau de Toilette (EDT)

| | | |
|---|---|---|
| Phase A | | |
| Alcohol | | ad 100 |
| Fragrance | | 15 |
| Benzophenone 2 | | 0.1 |
| Phase B | | |
| Water | | 3.6 |
| Phase C | | |
| Alcohol | | 10 |
| Watertight complex* | | 3 |
| Phase D | | |
| Colorant | | 0.3 |

*see ex. 2

Mix separate prepared phases A and B. Mix alcohol and Hydrolyzed Jojoba Esters. Sprinkle in Acrylates/Octylacrylamide Copolymer while mixing and mix until clear and uniform. Add phase C to the main batch and after that phase D. Mix until uniform.

EXAMPLE 12

Clear Deodorant Stick

| | | |
|---|---|---|
| Phase A | | |
| Propylene Glycol | | ad 100 |
| Sodium Stearate | | 6.5 |
| Isosteareth-20 | | 5 |
| Steareth-2 | | 1 |
| Phase B | | |
| 10% NaOH Sol | | 0.1 |
| Water | | 14.5 |
| Watertight complex* | | 0.5 |
| Phase C | | |
| Fragrance | | 1.5 |
| Colorant | | 0.4 |

*see ex. 2

EXAMPLE 13

Perfume

| | | |
|---|---|---|
| Phase A | | |
| Alcohol | | 65 |
| Benzophenone-2 | | 0.1 |
| Fragrance | | 13.5 |
| Phase B | | |
| Water | | ad 100 |
| Phase C | | |
| Colorant | | 1.0 |
| Phase D | | |
| Dermacryl ® AQF | | 10 |
| Hydrolyzed Jojoba Esters | | 5 |

Phases A and B are mixed and filtered. Phase C is added while mixing. Separately prepared phase D is added to the main batch and mixed until clear and uniform.

EXAMPLE 14

Perfume

| Phase A | |
|---|---|
| Alcohol | 55 |
| Benzophenone-2 | 0.1 |
| Fragrance | 20 |
| Phase B | |
| Water | ad 100 |
| Phase C | |
| Alcohol | 10 |
| Dermacryl ® AQF | 3.3 |
| Hydrolyzed Jojoba Esters | 1.7 |
| Colorant | 1.0 |

Phases A and B are mixed and filtered. Separately prepared phase C is added to the main batch and mixed until clear and uniform.

Phase C is added while mixing.

EXAMPLE 15

Comparative Test I

Comparative tests were carried out using the composition according to Example 1 (Sample A) and the same composition without the ingredients of Phase D (Sample B).

Two drops (approx. 0.3 g) of each sample were dropped on to the inner side of the right or left forearm of the test person. The drying time was 15 minutes. Two hours later, the forearm was immersed in water having a temperature of 26° C. for 4 minutes. The forearm was then dried in the air. The immersion and drying process was repeated after 4 and 6 hours, rinsing the water container and changing the water in the container before each immersion.

Figure 2:
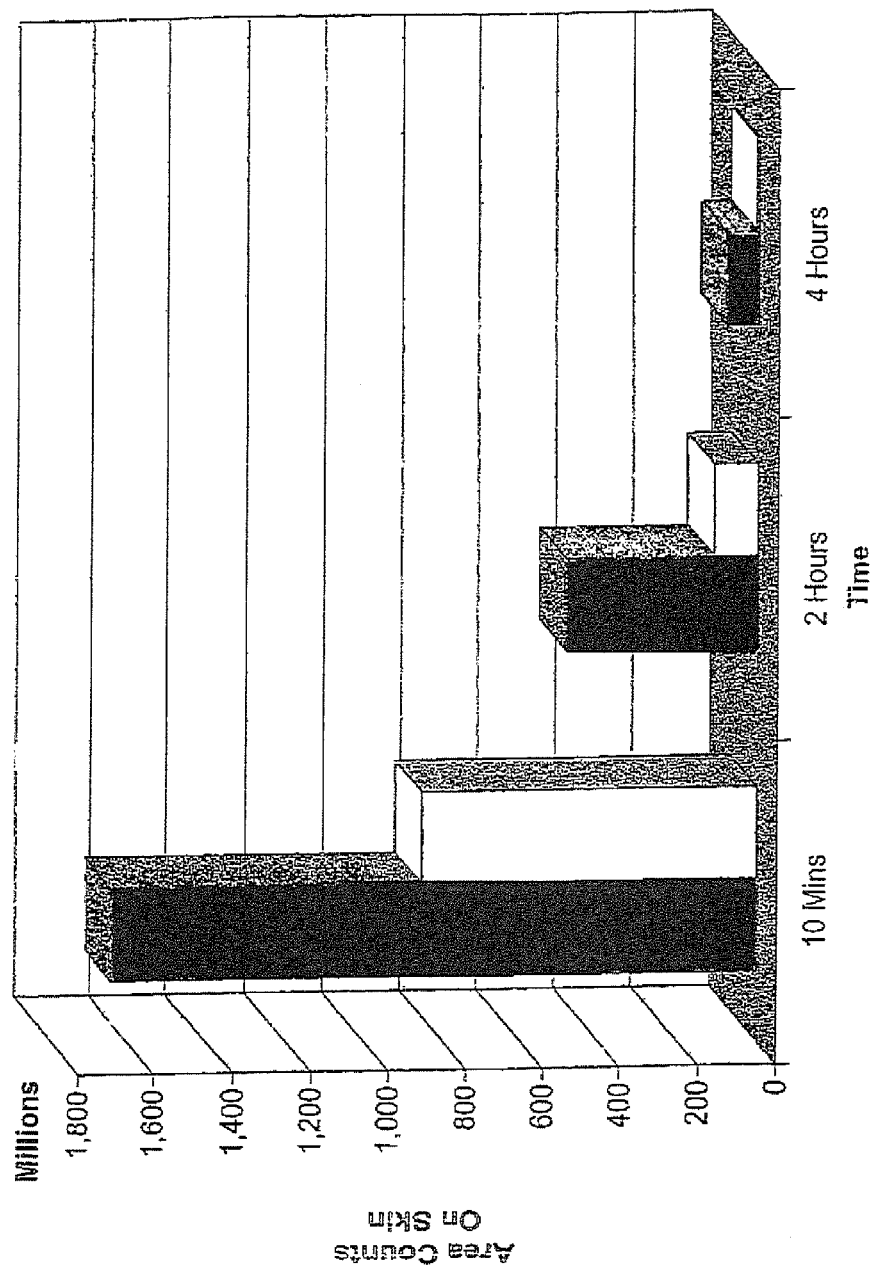
FIG. 2: Analytical results of aftershave of example 1
Figure 3:
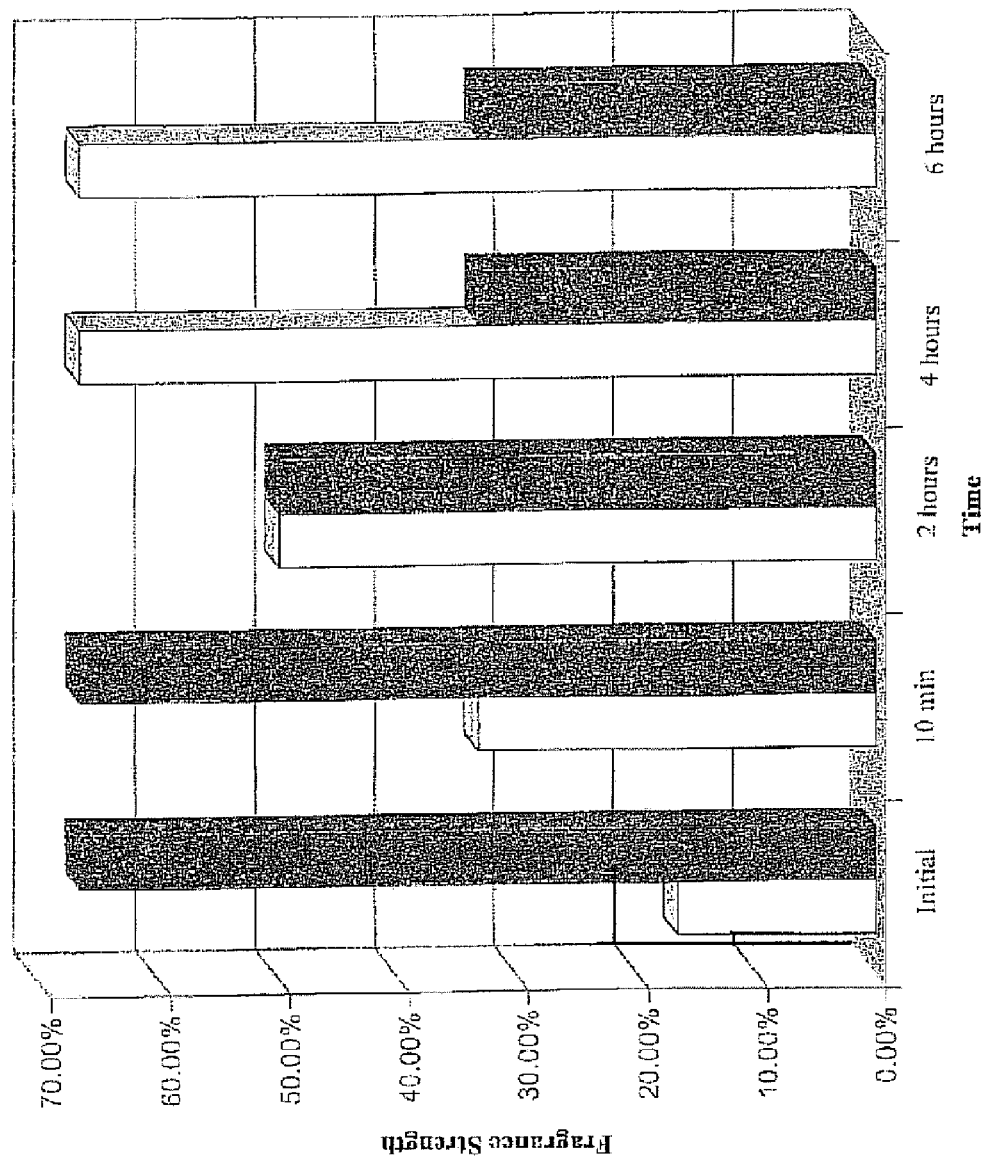
FIG. 3: Sensory analysis of EDT of example 11

In a sensory test performed with 4 experienced testers, a result according to FIG. 1 was obtained. The same samples were analysed by means of gas chromatography/mass spectroscopy and the diagram according to FIG. 2 was obtained. The results were achieved by SPME (see example 16 part B). Both results demonstrate that the waterproofness is considerably increased.

In a comparative test using a EDT according to Example 11 (Sample C but with 0.5% complex only) and the same EDT without the complex of copolymer and jojoba ester (Sample D), the waterproofness determined by means of a long-time sensory test was found to be more than twice the values of the same EDT without the complex according to the invention after 6 hours. A similar test using an aftershave demonstrated this superiority in a sensory test even after 8 hours.

EXAMPLE 16

Comparative Test II

Part A

Comparative tests were carried out to demonstrate the ability of the complex of the invention to reduce the fragrance content in a perfume.

Two perfumes were produced. Perfume C had the following ingredients (in % by weight): 72.7% Alcohol, 0.5% Diisopropyl Adipate, 0.5% C12-C15-Alkyl Lactate, 12% Fragrance, 14.3% Water. Perfume C1: the first three ingredients were the same as in Perfume C but with 9.6% Fragrance, 15.3% Water, 1% complex of example 2, 0.4% $Na_2O_3$ solution (10%).

A group of 20 panelists were asked to identify the different fragrance shares in perfume C and perfume C1. Three panelists identified the different fragrances correctly, 17 did not.

The same results were obtained with a reduction of fragrance from 16% to 12.8% and from 15% to 12% respectively (each with 1% of the complex in the formula with the reduced fragrance share).

Part B SPME Test

Solid-phase micro extraction (SPME) is a method in which analytes partition from a sample into a polymer, coated on a fused silica rod of typically 1 cm length by 100 μm diameter. The fiber is fastened into the end of a fine stainless steel tube contained in a syringe-like device and protected by an outer stainless steel needle. The device's plunger is depressed to expose the fiber to the sample matrix, retracted at the end of the sampling time, and then depressed again to expose the fiber to a desorption interface for analysis, in this case by Gas Chromatography. Reference is made to ex. 2 of US 2002/0192174 A1.

Figure 4:
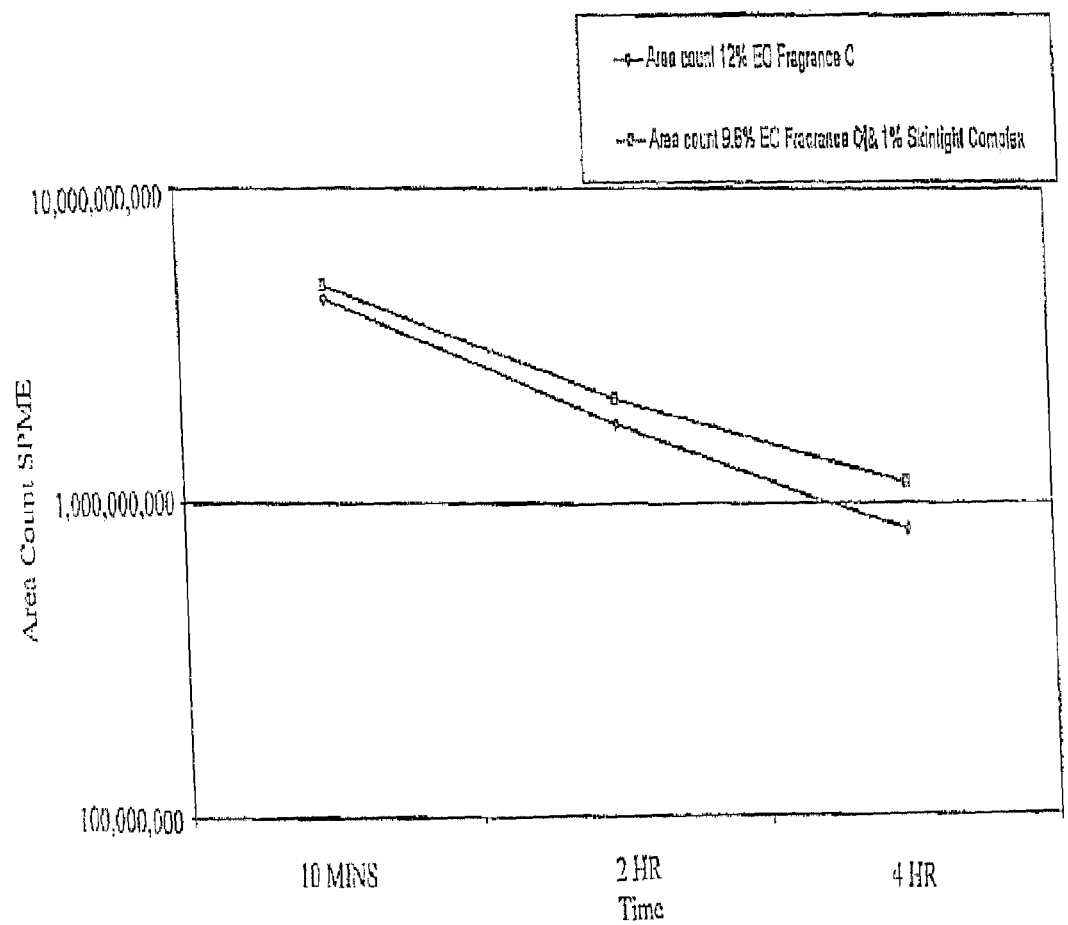
FIG. 4: SPME results for fragrance C (ex. 16) skintight headspace All quantities in the examples are given in percent by weight unless indicated otherwise.

The result of the GC measurement is presented in FIG. 4 with 12% perfume C and 9.6% perfume C1 including 1% of the watertight skintight complex according to example 2. Both perfumes show nearly the same area counts. This confirms the results of the consumer test of part A.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 2004 005 095.3, filed Jan. 27, 2004, and U.S. Provisional Application Ser. No. 60/600,018, filed Aug. 9, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method of providing water-resistant fragrance, the method comprising:
   applying to skin a cosmetic composition with a watertight fragrance, the composition comprising: a) one or more fragrances, and b) 0.1 to 15% by weight of a fragrance-fixing complex consisting of 0.01 to 10% by weight of a hydrophobic, alcohol-soluble, carboxylated acrylates/octylacrylamide copolymer and 0.01 to 10% by weight of a hydrolyzed jojoba ester, such that the one or more fragrances are resistant to wash off by water and sweat and remain fixed on the skin, wherein all percents are related to the total weight of the cosmetic composition,
characterized in that
the fragrance-fixing complex is formed prior to addition of the fragrance by spraying at a temperature of 18° to 25° C. the acrylates/octylacrylamide copolymer in powder form into a mixture consisting of the hydrolyzed jojoba ester and an alcohol or an alcohol/water mixture wherein the complex is dried before use in said cosmetic composition.

2. The method of claim 1, wherein the composition further comprises an alcohol or an alcohol/water mixture.

3. The method of claim 1, wherein the amount of the copolymer is in the range of 0.1 to 5% by weight.

4. The method of claim 3, wherein the amount of the copolymer is in the range of 0.1 to 1% by weight.

5. The method of claim 1, wherein the amount of the jojoba ester is in the range of 0.1 to 5% by weight.

6. The method of claim 5, wherein the amount of the jojoba ester is in the range of 0.1 to 1% by weight.

7. The method of claim 1, wherein said one or more fragrances are present in an amount ranging between 0.01 and 35% by weight.

8. The method of claim 7, wherein said one or more fragrances are present in an amount ranging between 0.1 and 16% by weight.

9. The method of claim 8, wherein said one or more fragrances are present in an amount ranging between 0.1 and 8% by weight.

10. The method of claim 1, wherein said hydrolyzed jojoba ester is derived from the plant *Simmondsia chinensis* and has a saponification value according to the American Oil Chemists Society test procedure ACOS Cd 3-25 of max. 1 mg KOH/g, a iodine value according to the American Oil Chemists Society test procedure ACOS Cd Id-92 of between 14 and 17 g/100 g and a trans isomer value according to the American Oil Chemists Society test procedure ACOS Cd 14-95 of max. 0.1% by weight.

11. The method of claim 1, wherein the complex is provided in a cosmetic product selected from perfumes, Eau de Toilettes, hair products, body care products, sun care products, antiperspirants, deodorants, detergents and products of color cosmetic.

12. The method of claim 1, wherein the amount of the complex in the cosmetic product is in the range of 0.5 to 10% by weight.

13. The method of claim 1, wherein the amount of the complex in the cosmetic product is in the range of 0.5 to 4% by weight.

14. The method of claim 1, wherein the amount of the complex in the cosmetic product is in the range of 0.5 to 1.5% by weight.

15. The method of claim 1, wherein the composition further comprises cosmetic auxiliaries, cosmetic actives, and carrier substances as commonly used in cosmetic compositions.

16. The method of claim 1, wherein the amount of the copolymer is in the range of 0.1 to 5% by weight, the amount of the jojoba ester is in the range of 0.1 to 5% by weight, and said one or more fragrances are present in an amount ranging between 0.01 and 35% by weight.

17. The method of claim 1, wherein the amount of the copolymer is in the range of 0.1 to 1% by weight, the amount of the jojoba ester is in the range of 0.1 to 1% by weight, and said one or more fragrances are present in an amount ranging between 0.1 and 16% by weight.

18. The method of claim 1, wherein said jojoba ester and said copolymer constitute a separately prepared complex in the relation 1:1-4 of jojoba ester:polymer.

19. The method of claim 1, wherein said jojoba ester and said copolymer constitute a separately prepared complex in the relation 1:1.2-2.8 of jojoba ester:polymer.

20. The method of claim 1, wherein said one or more fragrances are oil-soluble fragrances.

21. The method of claim 1, wherein the amount of the complex is in the range of 0.5-8% by weight, relative to the total weight of the cosmetic composition.

22. The method of claim 1, wherein the amount of the complex is in the range of 1-3% by weight, relative to the total weight of the cosmetic composition.

* * * * *